United States Patent [19]
Znaiden et al.

[11] Patent Number: 5,814,662
[45] Date of Patent: Sep. 29, 1998

[54] SKIN TREATMENT WITH ALPHA-HYDROXYCARBOXYLIC ACIDS OF MIXED CHAIN LENGTH

[75] Inventors: Alexander Paul Znaiden, Trumbull; Brian Andrew Crotty, Branford; Anthony Johnson, Fairfield, all of Conn.

[73] Assignee: Chesebrough-Pond's USA Co., Division of Conopco, Inc., Greenwich, Conn.

[21] Appl. No.: 742,990

[22] Filed: Nov. 1, 1996

[51] Int. Cl.[6] ............ A01N 37/00; A61K 31/19
[52] U.S. Cl. ............ 514/557; 514/844; 514/847; 514/873
[58] Field of Search .................. 514/557, 844, 514/847, 873

[56] References Cited

U.S. PATENT DOCUMENTS

| | | | |
|---|---|---|---|
| 5,091,171 | 2/1992 | Yu et al. | 424/642 |
| 5,556,970 | 9/1996 | Kawasaki et al. | 554/190 |

*Primary Examiner*—S. Mark Clardy
*Assistant Examiner*—Michael A. Williamson
*Attorney, Agent, or Firm*—Milton L. Honig

[57] ABSTRACT

A cosmetic composition is provided which includes a $C_2$–$C_4$ alpha-hydroxycarboxylic acid and a $C_{16}$–$C_{20}$ alpha-hydroxycarboxylic acid delivered in a pharmaceutically acceptable carrier. Most preferred as the longer chain acids is a mixture fractionated from lanolin. The cosmetic composition can be employed in a method for treating dermatological disorders, chronoaging and environmental abuse. Preferably the composition is intended to inhibit or reduce the formation of wrinkles and sagging of skin while improving glow and firmness.

11 Claims, No Drawings

SKIN TREATMENT WITH ALPHA-HYDROXYCARBOXYLIC ACIDS OF MIXED CHAIN LENGTH

BACKGROUND OF THE INVENTION

1. Field of the Invention

The present invention concerns compositions containing alpha-hydroxycarboxylic acids and methods for improving skin conditions by topical application of these compositions.

2. The Related Art

Skin is subject to deterioration through dermatologic disorders or normal aging (chronoaging) as well as extrinsic factors (environmental). Dermatologic disorders include such conditions as acne, dry skin, dandruff, keratosis, pruritus, inflammatory dermatoses, eczema, psoriasis and tinea pedis (athlete's foot).

Chronoaging results in the thinning and general degradation of skin. As skin naturally ages, there is reduction in the cells and blood vessels that supply the skin. There is also a flattening of the dermal-epidermal junction which results in weaker mechanical resistance. Older individuals increasingly develop facial fine lines, wrinkles, leatheriness, yellowing, sagging, mottling (hyperpigmentation), age spots, reduced glow, loss of firmness and the general signs of aging.

Extrinsic factors are primarily those caused by exposure to sun. Changes are most prominent in light skinned individuals who burn easily and tan poorly. The results of photodamage may be identical to those of aging except appearing at an accelerated rate. Wrinkling, yellowing, leatheriness, mottling and hyperpigmentation are all associated with sun damage. Most disturbing to many individuals is the wrinkling effect. It is a prime reminder of the disappearance of youth. As a result, there have been many reports of cosmetic treatments aimed at the elimination of wrinkles.

U.S. Pat. No. 5,091,171 (Yu et al.) discloses use of alpha-hydroxycarboxylic acids for use in alleviating both cosmetic conditions and dermatological disorders including those of dry skin, dandruff, acne, keratosis, psoriasis, eczema, pruritus, age spots, wrinkles, warts, blemishes, hyperpigmentation, hyperkeratotic skin, inflammatory dermatoses and changes associated with skin aging.

Combinations of different alpha-hydroxycarboxylic acids have been exploited commercially. Pond's® Age Defying Cream has been sold for many years with a composition including glycolic acid and alpha-hydroxycaprylic acid. This and related products have achieved cosmetic improvements in sags, wrinkles, glow and firmness of skin. Nevertheless there is still a great need for much further improvements.

Accordingly it is an object of the present invention to provide compositions and a treatment for a variety of dermatologic disorders such as acne, dry skin, dandruff, keratosis, pruritus, inflammatory dermatosis, eczema, psoriasis and tinea pedis.

Another object of the present invention is to provide compositions and a treatment for chronoaging conditions such as wrinkling and fine lines, leatheriness, yellowing, sagging, mottling (hyperpigmentation), age spots and the general signs of aging.

Still another object of the present invention is to provide compositions and a treatment against environmental abuses to skin such as those resulting in wrinkling and fine lines, yellowing, leatheriness, mottling and hyperpigmentation.

Yet another object of the present invention is to provide compositions and a treatment to improve the general tone, glow and firmness of skin resulting from the aging process.

These and other objects of the present invention will become more readily apparent from the following summary and detailed discussion.

SUMMARY OF THE INVENTION

A cosmetic composition has been provided which includes:

(i) from 0.01 to 15% by weight of a $C_2$–$C_4$ alpha-hydroxycarboxylic acid;

(ii) from 0.01 to 15% by weight of a $C_{16}$–$C_{20}$ alpha-hydroxycarboxylic acid; and (iii) from 1 to 99.9% of a pharmaceutically acceptable carrier.

A method is also provided for treating skin conditions selected from the group consisting of dermatologic skin disorders, chronoaging, environmental abuse and combinations thereof, by applying to the skin the cosmetic composition as hereinabove described.

DETAILED DESCRIPTION OF THE INVENTION

Now it has been discovered that deterioration of skin through dermatologic disorders, chronoaging and environmental abuse (e.g. sun and wind) can be reduced, inhibited and even reversed through application of a cosmetic composition including a combination of short and long chain alpha-hydroxycarboxylic acids. Particularly the combination includes a $C_2$–$C_4$ alpha-hydroxycarboxylic acid with a $C_{16}$–$C_{20}$ alpha-hydroxycarboxylic acid delivered in a pharmaceutically acceptable carrier.

Short chain acids suitable for the present invention are glycolic and lactic acids. Illustrative of the long chain acids are alpha-hydroxyhexadecanoic acid, alpha-hydroxyoctadecanoic acid and alpha-hydroxybehenoic acid as well as combinations thereof. Amounts each for short and long chain acids may range from 0.01 to 15%, preferably from 0.5 to 12%, more preferably from 1 to 10% by weight. A source most preferred for the long chain type is that derived from the fractionation (e.g. via distillation or chromatography) of lanolin. The preferred fraction mainly contains $C_{16}$ and $C_{18}$ alpha-hydroxycarboxylic acids in ratios varying from 10:1 to 1:10, preferably 8:1 to 1:1, optimally from 5:1 to 2:1, respectively. Croda Oleochemicals, England, is a commercial source for the lanolin fractions. These fractions may also contain a homologous series of normal, iso and anteiso aliphatic acids, omega hydroxy acids and oligomeric esters, Within the context of the present invention, the term alpha-hydroxycarboxylic acid is defined to include not only the free acid form but also salts such as the alkali metal, ammonium and alkanolammonium salts.

Besides the active alpha-hydroxycarboxylic acids, compositions of the present invention will utilize a pharmaceutically acceptable carrier. The carrier may either be aqueous, anhydrous or an emulsion. Preferably the compositions are aqueous, especially water and oil emulsions of the W/O or O/W variety. Water when present will be in amounts which may range from 5 to 95%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 25 to 40% by weight.

Emollient materials may also serve as pharmaceutically acceptable carriers. These may be in the form of silicone oils and synthetic esters. Amounts of the emollients may range anywhere from 0.1 to 30%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Fatty acids having from 10 to 30 carbon atoms may also be included as pharmaceutically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type can be employed as pharmaceutically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners can be utilized as part of the pharmaceutically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenum, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the pharmaceutically acceptable carrier in amounts from 1 to 99.9%, preferably from 80 to 99% by weight.

Cosmetic compositions of the present invention may be in any form. These forms may include lotions, creams, roll-on formulations, mousses, aerosol and non-aerosol sprays and pad-applied formulations.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, $C_8$–$C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain water-soluble vitamins. The term water-soluble defines substances with a solubility of at least 0.1%, preferably at least 1%, optimally at least 5% by weight in water. Illustrative water-soluble vitamins are Niacin, Vitamin $B_2$, Vitamin $B_6$, Vitamin C and Biotin. One source for Vitamin C is a product sold under the trademark of Vitazyme C available from the Brooks Company. Niacin, Vitamin B and Biotin are available from Roche Pharmaceuticals. Total amount of vitamins in compositions according to the present invention may range from 0.001 to 1%, preferably from 0.01 to 0.6, optimally from 0.1 to 0.5% by weight.

Minor adjunct ingredients may also be present in the cosmetic compositions. Among them may be the water-insoluble vitamins such as Vitamin A Palmitate, Vitamin E Acetate and DL-panthenol.

Another adjunct ingredient can be that of an enzyme. Particularly preferred is superoxide dismutase, commercially available as Biocell SOD from the Brooks Company, USA.

Natural vegetable materials from renewable resources are often desirable in cosmetic compositions. For instance, cosmetic compositions of the present invention may include β-glucan derived from oats, commercially available under the trademark Microat SF from Nurture Inc., Missoula, Mont.

Colorants, fragrances, opacifiers and abrasives may also be included in compositions of the present invention. Each of these substances may range from about 0.05 to about 5%, preferably between 0.1 and 3% by weight.

The following Examples will more fully illustrate embodiments of this invention. All parts, percentages and proportions referred to herein and in the appended claims are by weight unless otherwise indicated.

EXAMPLE 1

A typical cosmetic composition according to the present invention has the following formula.

TABLE I

| COMPONENT | WEIGHT % |
|---|---|
| Glycolic Acid (70%) | 5.74 |
| Alpha-Hydroxyhexadecanoic Acid | 3.00 |
| Butylene Glycol | 3.00 |
| Stearic Acid | 3.00 |
| Finsolv TN ® | 2.50 |
| Ceraphyl 230 ® | 2.50 |
| Ammonia (Aqueous 26BE) | 2.20 |
| Glycerin | 2.00 |
| Myrj 59 ® | 2.00 |
| Polyethylene Imine | 2.00 |
| Stearyl Alcohol | 1.50 |
| Glycerol Monostearate | 1.50 |
| Triethanolamine (99%) | 1.20 |
| Magnesium Aluminum Silicate | 1.00 |
| SE 700 | 1.00 |
| Silicone Fluid 10 | 1.00 |
| Arlacel 60 ® | 1.00 |
| Dow Corning 1401 ® | 0.80 |
| Jaguar HP-120 ® | 0.50 |
| Disodium EDTA | 0.50 |

TABLE I-continued

| COMPONENT | WEIGHT % |
|---|---|
| Sodium Stearoyl Lactylate | 0.50 |
| Cholesterol | 0.30 |
| Fragrance | 0.30 |
| Tween 80 ® | 0.30 |
| Methylparaben | 0.15 |
| Antifoam Emulsion | 0.10 |
| Vitamin E Acetate | 0.10 |
| Propylparaben | 0.10 |
| Hydroxycaprylic Acid | 0.10 |
| Vitamin A Palmitate | 0.10 |
| Bisabolol | 0.10 |
| Water | qs |

EXAMPLE 2

Another cosmetic composition according to the present invention has the formula as listed below.

TABLE II

| COMPONENT | WEIGHT % |
|---|---|
| Propylene Glycol Isoceteth-3 Acetate | 14.00 |
| Octyl Dodecyl neopentanoate | 14.00 |
| Potassium L-Lactate | 13.00 |
| Parsol MCX ® | 5.00 |
| Parsol 1789 ® | 4.00 |
| Lanolin Extract ($C_{14}$–$C_{22}$ AHA Fraction) | 4.00 |
| Zinc Oxide | 3.00 |
| Dimethicone Copolyol Phosphate | 3.00 |
| PEG-20 Sorbitan Isostearate | 2.00 |
| Isostearic Acid | 1.75 |
| Polyoxyethylene (21) Stearyl Ether | 1.50 |
| Magnesium Aluminum Silicate | 0.70 |
| Propylene Glycol | 0.50 |
| Glycerin | 0.50 |
| Triethanolamine | 0.35 |
| Xanthan Gum | 0.20 |
| Polyoxyethylene (2) Stearyl Ether | 0.20 |
| Glydant Plus ® | 0.20 |
| Fragrance | 0.20 |
| Botanical Blend | 0.10 |
| Vitamin E Linoleate | 0.10 |
| Aloe Vera Gel | 0.01 |
| Water | qs |

EXAMPLE 3

A still further cosmetic composition illustrating the present invention is provided in the following formulation.

TABLE III

| COMPONENT | WEIGHT % |
|---|---|
| L-Lactic Acid | 7.00 |
| Alpha-Hydroxyoctadecanoic Acid | 4.00 |
| Triethanolamine | 3.00 |
| Alkyl Polyglycoside | 3.00 |
| Cetyl Alcohol | 2.50 |
| Glycerol Monostearate | 2.00 |
| Octyl Palmitate | 2.00 |
| Silicone Fluid | 1.50 |
| Petroleum Jelly | 1.00 |
| Methyl Paraben | 0.15 |
| Propyl Paraben | 0.10 |
| Fragrance | 0.10 |
| Antifoam | 0.01 |
| Water | qs |

EXAMPLE 4

Still another of cosmetic composition according to the present invention is that provided in the formula below.

TABLE IV

| COMPONENT | WEIGHT % |
|---|---|
| Alpha-Hydroxybehenoic Acid | 8.00 |
| Isopropyl Myristate | 3.00 |
| Stearic Acid | 3.00 |
| Propylene Glycol | 3.00 |
| Cyclomethicone | 3.00 |
| L-Lactic Acid | 2.00 |
| Panthenol | 1.00 |
| Ammonia (Aqueous 26 BE) | 1.00 |
| Disodium EDTA | 0.10 |
| Fragrance | 0.10 |
| Sodium Sorbate | 0.10 |
| Water | qs |

EXAMPLE 5

Yet another cosmetic composition illustrative of the present invention has the formula provided below.

TABLE V

| COMPONENT | WEIGHT % |
|---|---|
| Cyclomethicone | 48.30 |
| Ethyl Alcohol | 24.70 |
| Isopropyl PPG-2 Isodeceth-7-carboxylate | 10.00 |
| Ammonium Glycolate | 7.00 |
| Potassium Alpha-hydroxyhexadecanoate | 5.50 |
| Propylene Glycol Dicaprylate/Dicaprate | 4.00 |
| Hydroxycaprylic Acid | 0.50 |

EXAMPLE 6

A further cosmetic composition according to the present invention has a formula in which 8% glycolic acid and 1% lanolin extract are included with a base formula provided below.

TABLE VI

| COMPONENT | WT. % |
|---|---|
| Isostearyl Palmitate | 6.00 |
| Butylene Glycol | 3.00 |
| $C_{12}$–$C_{15}$ Alkyl Octanoate | 3.00 |
| Stearic Acid | 3.00 |
| Glycerin | 2.00 |
| PEG-100 Stearate | 2.00 |
| Glycerol Hydroxystearate | 1.50 |
| Stearyl Alcohol | 1.50 |
| Triethanolimine | 1.20 |
| Dimethicone | 1.00 |
| Sorbitan Stearate | 1.00 |
| Magnesium Aluminum Silicate | 0.60 |
| Hydroxyethylcellulose | 0.50 |
| Sodium Stearoyl Lactylate | 0.50 |
| Cholesterol | 0.50 |
| Bisabolol | 0.20 |
| Xanthan Gum | 0.20 |
| Methylparaben | 0.15 |
| Propylparaben | 0.10 |
| Vitamin E Acetate | 0.10 |
| Hydroxycaprylic Acid | 0.10 |
| Vitamin A Palimitate | 0.10 |
| Butylated Hydroxytoluene | 0.05 |
| Disodium EDTA | 0.05 |
| Fragrance | 0.03 |
| Water | balance |

EXAMPLE 7

This example reports on tests evaluating the effectiveness of the combined short and long chain acid compositions. A Living Skin Equivalent (LSE) test was used as an in vitro predictive tool demonstrating the activity of skin against chronoaging as well as against extrinsic factors. Most especially, this is a predictive tool for activity against wrinkles, sags and the improvement of skin glow and firmness.

The LSE used in this study was the "$Skin^2 ZK1300$" test from Advance Tissue Sciences, Inc., of La Jolla, Calif.

The test protocol was as follows.

| | |
|---|---|
| Model: | $Skin^2$ Model ZK1300 (13 days old) |
| Mode: | Topical application - 8 $\mu$l |
| Exposure: | 60 minutes/day for 3 consecutive days |
| Endpoints: | Proline incorporation |
| Dosing: | Full-strength dosing in triplicate once a day. |

Test materials were applied undiluted in triplicate onto the epidermal side of tissues. After application, tissues were incubated for 60 minutes. Next they were rinsed and placed onto plates containing radio active proline. On day one and day two they were placed back in the incubator for the night.

On the third day tissues were washed and count activity was determined using a Beckman Scintillation counter.

Tissues dosed with test agent were compared to untreated controls to determine the overall effect of the actives. Each of the actives was incorporated into a base cosmetic formula as identified under Table VI of Example 6 with the addition of ample base adjust the pH of the formula to the range of 3.8–5.2.

TABLE VII

| ACTIVE MATERIAL | % PROLINE INCORPORATION | | |
|---|---|---|---|
| Control (untreated) | 100 | | |
| 8% Glycolic Acid | 150 | | |
| 6% Lanolin Extract* | 215 | | |
| 4% Glycolic Acid/3% Lanolin Extract | 280 | | |
| *Alpha-Hydroxy Acid Content (30% of Fraction): | $C_{14}$ | 1.71% |
| | $C_{15}$ | 0.72 |
| | $C_{16}$ | 20.19 |
| | $C_{17}$ | 0.53 |
| | $C_{18}$ | 6.67 |
| | $C_{20}$ | 0.36 |
| | $C_{22}$ | 0.19 |

The results reported in Table VI shows that the lanolin extract fraction was more effective than glycolic acid. Most effective was a combination of glycolic acid and lanolin extract.

The foregoing description and Examples illustrate selected embodiments of the present invention. In light thereof, various modifications will be suggested to one skilled in the art, all of which are within the spirit and purview of this invention.

What is claimed is:

1. A cosmetic composition comprising:
    (i) from 0.01 to 15% by weight of a $C_2$–$C_4$ alpha-hydroxycarboxylic acid;
    (ii) from 0.01 to 15% by weight of a mixture of $C_{16}$ and $C_{18}$ alpha-hydroxycarboxylic acids in a relative weight ratio from 5:1 to 2:1; and
    (iii) from 1 to 99.9% of a pharmaceutically acceptable carrier.

2. The cosmetic composition according to claim 1 wherein the $C_{16}$ and $C_{18}$ alpha-hydroxycarboxylic acid is a mixture of acids obtained from fractionation of lanolin.

3. The cosmetic composition according to claim 1 wherein the $C_2$–$C_4$ alpha-hydroxycarboxylic acid is selected from the group consisting of glycolic acid and lactic acid.

4. A method for treating skin conditions selected from the group consisting of dermatological disorders, chronoaging and environmental abuse, the method comprising applying to the skin a safe and effective amount of a cosmetic composition comprising:
   (i) from 0.01 to 15% by weight of a $C_2$–$C_4$ alpha-hydroxycarboxylic acid;
   (ii) from 0.01 to 15% by weight of a mixture of $C_{16}$ and $C_{18}$ alpha-hydroxycarboxylic acids in a relative weight ratio from 5:1 to 2:1; and
   (iii) from 1 to 99.9% of a pharmaceutically acceptable carrier.

5. The method according to claim 4 wherein the dermatologic disorders are selected from the group consisting of acne, dry skin, dandruff, keratosis, pruritus, inflammatory dermatitis, eczema, psoriasis and tinea pedis.

6. The method according to claim 4 wherein the chronoaging is characterized by a condition selected from the group consisting of wrinkling, fine lines, leatheriness, yellowing, sagging, hyperpigmentation, age spots and general signs of aging.

7. The method according to claim 4 wherein environmental abuse includes conditions selected from the group consisting of wrinkling, fine lines, leatheriness, yellowing, mottling and hyperpigmentation.

8. A method for treating skin conditions selected from the group consisting of dermatological disorders, chronoaging and environmental abuse, the method comprising applying to the skin a safe and effective amount of a cosmetic composition comprising a $C_2$–$C_4$ alpha hydroxycarboxylic acid and a mixture of $C_{16}$ and $C_{18}$ alpha-hydroxycarboxylic acids in a weight ratio ranging from 5:1 to 2:1 and a pharmaceutically acceptable carrier.

9. The method according to claim 8 wherein the dermatologic disorders are selected from the group consisting of acne, dry skin, dandruff, keratosis, pruritus, inflammatory dermatitis, eczema, psoriasis and tinea pedis.

10. The method according to claim 8 wherein the chronoaging is characterized by a condition selected from the group consisting of wrinkling, fine lines, leatheriness, yellowing, sagging, hyperpigmentation, age spots and general signs of aging.

11. The method according to claim 8 wherein environmental abuse includes conditions selected from the group consisting of wrinkling, fine lines, leatheriness, yellowing, mottling and hyperpigmentation.

* * * * *